United States Patent
Folkerts et al.

(10) Patent No.: US 12,083,356 B2
(45) Date of Patent: Sep. 10, 2024

(54) MODEL BASED PBS OPTIMIZATION FOR FLASH THERAPY TREATMENT PLANNING AND ONCOLOGY INFORMATION SYSTEM

(71) Applicants: Varian Medical Systems, Inc., Palo Alto, CA (US); Varian Medical Systems International AG, Steinhausen (CH); Varian Medical Systems Particle Therapy GmbH & Co. KG, Troisdorf (DE)

(72) Inventors: Michael Matthew Folkerts, Carrollton, TX (US); Jessica Perez, Geneva (CH); Christel Smith, Santa Barbara, CA (US); Eric Abel, San Jose, CA (US); Anthony Magliari, Newark, IL (US); Reynald Vanderstraeten, Uccle (BE); Timo Kalevi Koponen, Espoo (FI); Renate Parry, Oakland, CA (US); Alexander Katsis, San Mateo, CA (US); Rajiv Dua, Manteca, CA (US); Michiko Alcanzare, Espoo (FI); Perttu Niemela, Espoo (FI); Matti Ropo, Turku (FI)

(73) Assignees: SIEMENS HEALTHINEERS INTERNATIONAL AG, Steinhausen (CH); VARIAN MEDICAL SYSTEMS PARTICLE THERAPY GMBH & CO. KG, Troisdorf (DE); VARIAN MEDICAL SYSTEMS INC, Palo Alto, CA (US)

( * ) Notice: Subject to any disclaimer, the term of this patent is extended or adjusted under 35 U.S.C. 154(b) by 338 days.

(21) Appl. No.: 17/383,345

(22) Filed: Jul. 22, 2021

(65) Prior Publication Data
US 2021/0346719 A1 Nov. 11, 2021

Related U.S. Application Data

(63) Continuation of application No. 16/438,174, filed on Jun. 11, 2019, now Pat. No. 11,103,727, which is a (Continued)

(51) Int. Cl.
*A61N 5/10* (2006.01)
*G06T 7/00* (2017.01)

(52) U.S. Cl.
CPC .......... *A61N 5/1031* (2013.01); *G06T 7/0012* (2013.01); *A61N 2005/1032* (2013.01); (Continued)

(58) Field of Classification Search
CPC .......... A61N 2005/1074; A61B 5/0037; A61B 5/1032; A61B 5/0036; A61B 5/1031;
(Continued)

(56) References Cited

U.S. PATENT DOCUMENTS

2020/0282233 A1* 9/2020 Folkerts ................. G16H 20/40
2020/0282234 A1* 9/2020 Folkerts ................. G06T 7/0012

* cited by examiner

*Primary Examiner* — Don K Wong
(74) *Attorney, Agent, or Firm* — Harness, Dickey & Pierce, P.L.C.

(57) ABSTRACT

A computing system comprising a central processing unit (CPU), and memory coupled to the CPU and having stored therein instructions that, when executed by the computing system, cause the computing system to execute operations to generate a radiation treatment plan. The operations include accessing a minimum prescribed dose to be delivered into and across the target, determining a number of beams and directions of the beams, and determining a beam energy for each of the beams, wherein the number of beams, the directions of the beams, and the beam energy for each of the beams are determined such that the entire target receives the minimum prescribed dose. A quantitative time-dependent
(Continued)

model-based charged particle pencil beam scanning optimization is then implemented for FLASH therapy.

22 Claims, 3 Drawing Sheets

Related U.S. Application Data continuation-in-part of application No. 16/297,448, filed on Mar. 8, 2019, now Pat. No. 11,090,508.

(52) U.S. Cl.
CPC ............... *G06T 2207/10076* (2013.01); *G06T 2207/30004* (2013.01)

(58) Field of Classification Search
CPC ...... A61B 5/1084; A61B 5/1042; A61K 9/51; A61K 45/06; A61K 35/00; G16H 20/40
See application file for complete search history.

MODEL BASED PBS OPTIMIZATION FOR FLASH THERAPY TREATMENT PLANNING AND ONCOLOGY INFORMATION SYSTEM

This Application is a Continuation of U.S. application Ser. No. 16/438,174, filed on Jun. 11, 2019, "A Model Based PBS Optimization for Flash Therapy Treatment Planning and Oncology Information System," by Michael Matthew Folkerts, et al., which is a Continuation-in-Part of commonly assigned, copending U.S. application Ser. No. 16/297,448, filed on Mar. 8, 2019, "System and Method for Biological Treatment Planning and Decision Support," by Michael Matthew Folkerts, et al., which are incorporated herein in their entirety.

FIELD OF THE INVENTION

Embodiments of the present invention generally relate to the field of radiotherapy. More specifically, embodiments of the present invention relate to computer-implemented treatment planning methods and systems for radiotherapy treatment.

BACKGROUND OF THE INVENTION

Radiotherapy treatment planning based on biological parameters is referred to in the art as biological planning. One goal of radiotherapy treatment and biological planning is to maximize the dose supplied to a target tumor while minimizing the dose absorbed by the surrounding (normal) tissue. Treatment outcome regarding tumor control and normal tissue toxicities not only depend on physical parameters, such as dose, but also depend on a multitude of biological parameters that may or may not be known at the time of treatment.

Radiotherapy treatment planning typically involves extracting data from in vitro experiments where cell lines are irradiated, and the cell survival curves are used to define alpha-beta ratios of different cell types. Probabilistic models of tumor control probability (TCP) and normal tissue complication probability (NTCP) are created and can be used for clinical decision making. However, the clinical relevance of TCP/NTCP models is uncertain and there is a low level of confidence in the community regarding the accuracy of the models and the predicted values thereof. Moreover, it remains unclear which biological inputs might be required in order to achieve effective biological planning and to support a decision to treat a specific patient in a specific manner.

Currently the inclusion of biological parameters in treatment planning and decision making is not integrated into treatment planning systems. Treatment plans are often solely based on physical dose and displayed in 3D. Any relevant biological knowledge correlating treatment plans to outcome is not evaluated or is achieved separately from plan quality dosimetry metrics. For example, most clinics only use dosimetric endpoint goals as a proxy for biological impact, such as, "do not exceed max spinal cord dose of x."

In order to use biological information to guide treatment decision using current techniques, physically recorded parameters, such as dose, have to be extracted from the treatment planning system, and outcome modeling must be built in-house separately for each research parameter that is under evaluation. This has resulted in several biological models for radiation therapy developed for research, none of which are clinically accepted for use in actual treatment planning. Moreover, the dose is typically visualized with a color wash map; however, there is currently no built-in display method to visualize user-defined biological input functions in a similar fashion.

For clinical research and clinical trials, there are very few tools that can allow a researcher to test biological models that correlate input (4-D physically measured/"known" quantities) in relation to the output (e.g., biological observables such as toxicities, cell damage as observed on a 3D computerized tomography (CT), or even patient reported outcomes). Additionally, there are few tools that allow the user to compile the inputs in a reasonable fashion for radiotherapy. One common problem is that users do not know which treatment plan to apply to a registry because different versions of the treatment plan may be adapted and modified over time. For example, one treatment plan (including the 3D dose distribution) can represent a snapshot of how the dose is deposited given a certain beam arrangement and/or beam parameters on the patient's anatomy at the moment the simulation CT was acquired. Therefore, the treatment plan and the dosimetric endpoints often serve the registry as the input, but this input entails a large degree of uncertainty.

In many cases, radiation can be delivered to the tumor with submillimeter precision while mostly sparing normal tissue, ultimately leading to tumor cell killing. However, the tumor cell's ability to escape the cell killing effects of radiation and/or to develop resistance mechanism can counteract the tumor cell killing action of radiotherapy, potentially limiting the therapeutic effect of radiotherapy to treat cancer. Furthermore, the potential for normal tissue toxicity can impact the therapeutic window of radiation therapy as a treatment paradigm. Delivery of ultra-high dose radiation is believed to spare normal tissue from radiation-induced toxicity, thus increasing the therapeutic window. However, the therapeutic window can be widened even more by combining ultra-high dose radiation with targeted drugs, or the use of biomarkers for patient stratification.

SUMMARY OF THE INVENTION

Embodiments of the present invention provide integrated solutions to radiotherapy treatment planning that enable accurate recording and accumulation of physical parameters as input (e.g., dose, dose rate, irradiation time per voxel, etc.). User-defined functions are evaluated to correlate the input parameters with 4D biological outcomes. The resulting biological parameters can be visualized on a computer display as a biological outcome map to evaluate decisions, support decisions, and optimize decisions regarding the parameters of the radiotherapy treatment plan, for example, for supporting clinical trials and related clinical research. Including biological information into the treatment planning system leads to biologically optimized treatment capable of using ultra-high dose radiation. Biological parameters can be included into treatment planning on a voxel-by-voxel basis and the results can be displayed as a biological map.

According to one embodiment, a computer-implemented method for radiotherapy treatment planning is disclosed. The method includes receiving physical input parameters, evaluating a treatment hypothesis to determine a relationship between the physical input parameters and a biological outcome, generating a biological outcome map using an input function based on the relationship, displaying the biological outcome map on a display device to visualize the relationship, and optimizing a radiotherapy treatment plan based on the relationship depicted in the biological outcome map.

According to some embodiments, the input function represents a biological model.

According to some embodiments, optimizing the radiotherapy treatment plan includes minimizing a dose delivered to normal tissue.

According to some embodiments, the computer-implemented method includes determining the biological outcome by analyzing a post-treatment image.

According to some embodiments, optimizing the radiotherapy treatment plan includes optimizing a physical dose and a biological dose of the radiotherapy treatment plan, and the method further includes assigning priority levels to the physical dose and the biological dose.

According to some embodiments the displaying the biological outcome map includes overlaying the biological outcome map on top of a 3D dose map.

According to some embodiments the biological outcome map includes a 3D image.

According to some embodiments the biological outcome map includes a 4D image that varies over time.

According to some embodiments the receiving physical input parameters includes accumulating the physical input parameters as 4D physical measurements.

According to some embodiments the physical input parameters are associated with voxels.

According to some embodiments the physical input parameters include at least one of a dose and a dose rate.

According to some embodiments the physical input parameters include at least one of an irradiation time and a beam overlap.

According to some embodiments the biological outcome includes a toxicity level.

According to some embodiments the biological outcome includes at least one of a systemic biomarker and a genetic biomarker.

According to another embodiment, a system for radiotherapy treatment planning is disclosed. The system includes a display, a memory and a processor in communication with the memory that executes instructions for performing a method of radiotherapy treatment planning. The method includes receiving physical input parameters, evaluating a treatment hypothesis to determine a relationship between the physical input parameters and a biological outcome, generating a biological outcome map using an input function based on the relationship, displaying the biological outcome map on a computer-controlled display device to visualize the relationship, and optimizing a radiotherapy treatment plan based on the relationship depicted in the biological outcome map.

According to another embodiment, a non-transitory computer-readable storage medium embodying instructions that are executed by a processor to cause the processor to perform a method of radiotherapy treatment planning is disclosed. The method includes receiving physical input parameters, evaluating a treatment hypothesis to determine a relationship between the physical input parameters and a biological outcome, generating a biological outcome map using an input function based on the relationship, displaying the biological outcome map on a computer-controlled display device to visualize the relationship, and optimizing a radiotherapy treatment plan based on the relationship depicted in the biological outcome map.

In one embodiment, the present invention is implanted as a computing system comprising a central processing unit (CPU), and memory coupled to the CPU and having stored therein instructions that, when executed by the computing system, cause the computing system to execute operations to generate a radiation treatment plan. The operations include accessing a minimum prescribed dose to be delivered into and across the target, determining a number of beams and directions of the beams, and determining a beam energy for each of the beams, wherein the number of beams, the directions of the beams, and the beam energy for each of the beams are determined such that the entire target receives the minimum prescribed dose. A quantitative time-dependent model-based charged particle pencil beam scanning optimization is then implemented for FLASH therapy.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTION

Figure 1:
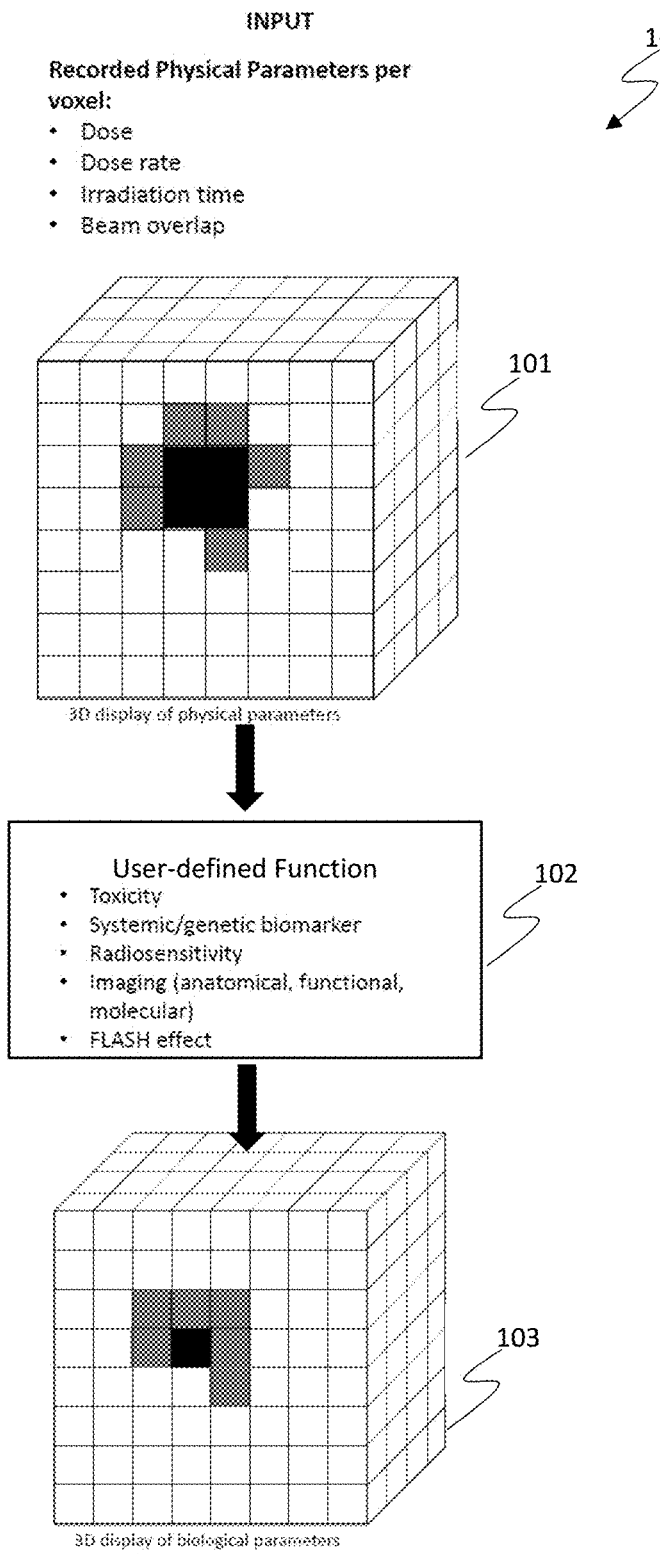
FIG. 1 is a diagram of an exemplary physical parameter input map and a resultant biological outcome map generated according to a user-defined function or model depicted according to embodiments of the present invention.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "directing," "controlling," "defining," "arranging," "generating," "representing," "applying," "adding," "multiplying," "adjusting," "calculating," "predicting," "weighting," "assigning," "using," "identifying," "reducing," "downloading," "reading," "computing," "storing," or the like, refer to actions and processes of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices. Terms such as "dose" or "fluence" generally refer to a dose or fluence value; the use of such terms will be clear from the context of the surrounding discussion.

Portions of the detailed description that follows are presented and discussed in terms of a method. Although steps and sequencing thereof are disclosed in figures herein describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

System and Method for Biological Treatment Planning and Decision Support

Embodiments of the present invention provide integrated solutions to radiotherapy treatment planning that enable accurate recording and accumulation of physical parameters as input (e.g., dose, dose rate, irradiation time per voxel, etc.). User-defined functions based on biological models are evaluated to correlate the input parameters with biological outcomes for biological planning. The biological parameters can be visualized on a computer screen as a biological outcome map to evaluate decisions, provide decision support, and optimize decisions regarding the parameters of a radiotherapy treatment plan, for example, for supporting clinical trials and related clinical research. Embodiments of the present invention can provide decision support for clinical trials by determining which arm of a trial a group of patients should be assigned to based on physical input parameters, such as elevated biomarkers, and by tracking the outcome results of the group of patients over time to evaluate a clinical research hypothesis.

A radiobiological equivalent (RBE) dose is a metric that takes biological parameters derived from experiments into consideration and modifies the dose by a specific factor. The modified dose then becomes the RBE dose and can be used for treatment planning and optimizations. Embodiments of the present invention advantageously enable treatment plans to be generated based on how the dose is affected by biological factors in addition to dosimetry. Moreover, embodiments of the present invention can be used as a research tool for evaluating various endpoints in addition to dose for clinical research and hypothesis evaluation. According to some embodiments, a software tool is executed by a computer system that takes known physical parameters as input, such as dose, per-voxel radiation time, and allows a user to test a clinical research hypothesis using the computer system. For example, a user can use the software tool to correlate the time a voxel has been irradiated with the toxicity in the voxel, and the result can be displayed on a computer screen as a 4D biological outcome map.

Embodiments of the present invention can evaluate a post-treatment image automatically using a computer system, where voxels of 3D physical parameters map are assigned toxicity scores based according to a hypothesis or biological model. Thereafter, the relationship (e.g., correlation) between the input and output, such as irradiation time and toxicity, can be visualized and/or quantified by rendering an image or video on a display device of the computer system. For example, the relationship can be used to define a function or model for generating a 3D map to visualize the relationship and assist treatment planning and optimization based on the correlated metric (e.g., irradiation time), in addition to a conventional dose map. According to some embodiments, the relationship between input and output is visualized as a 4D video map that includes a 3D image that changes over time. A time component is evaluated to generate the 4D video map of events occurring over time, and the 4D video is rendered on a display device of the computer system.

According to some embodiments, biological parameters for a treatment plan are defined on a per-voxel basis using a treatment planning tool, and a biological outcome map is generated according to a function or model and displayed to the user. Tumor control probability (TCP) planning and normal tissue complication probability (NTCP) planning generated in this way may include any user-defined biological parameters relevant to treatment planning in an integrated system, and the metric is rendered in 3D or 4D to track plan adaptions and accumulate the actual delivered dose. In this way, the user can automatically visualize and quantify relationships and/or correlations arising from research hypotheses and support treatment planning and optimization decisions using the computer-implemented treatment planning tool.

Moreover, the treatment planning tool disclosed herein can track or receive known 3D doses calculated during a simulation phase and overlay or otherwise visualize biological models to perform biological evaluation based on the calculated doses. The tool can simultaneously optimize physical dose and biological dose and determine the priority to assign to either biology or the physical dose. In this way, the computer-implemented tool can evaluate biological models in the treatment planning evaluation stage and incorporate biological factors into the plan optimization process. For example, biological planning can be layered on top of the physical dose optimization to visualize the relationship between input and output.

According to some embodiments, radiation treatment is combined with immune modulators to improve both the efficacy of radiation—both locally and systemically—as well as the efficacy of immune modulators. The radiation-immune modulator combination approach may require delivery of an ultra-high dose radiation to the tumor, knowledge of optimal dosing and sequence based on the immune modulators mechanism of action, fractionation pattern, and location of the primary tumor to ultimately achieve an optimal response. Furthermore, ultra-high dose radiation may facilitate the infiltration of immune cells deep into the core of the tumor, thus converting an immune desert into an immunological active tumor, thus potentially improving the efficacy of immune modulatory approaches. For example, radiation-induced tumor cell death leads to release of tumor antigens from lysed cells, increased MHC-1 expression on antigen presenting cells, and enhanced diversity of the intratumoral T-cell population. These factors (among others) are key to initiate activation of the body's own immune systems to eradicate cancer cells. Immune modulators are being explored to activate the body's own immune system, but are known to have limitations as monotherapy (e.g., response rate in patients). Therefore, embodiments of the present invention can incorporate check point inhibitors, co-stimulators, broad immune modulators, and chemokine inhibitors, and inhibitors of macrophage migration, for example.

With regard to FIG. 1, a diagram 100 of an exemplary physical parameter input map 101 and a resultant biological outcome map 103 generated according to a user-defined function or model 102 (e.g., clinical hypothesis) is depicted according to embodiments of the present invention. Such maps can be realized as data stored in computer memory and rendered for visualization by a computer on a display or printer. Embodiments of the present invention enable the accumulation of input data in a more accurate fashion compared to typical research hypothesis testing, where users must first extract physical parameters from a tissue polypeptide specific antigen (TPS) and build custom code in a different environment for testing the research hypothesis, for identifying important correlations, and for inputting the data back into the TPS. The input data 101 can include, but is not limited, to 3D input data such as dose accumulation from daily dose calculations based on cone beam computed tomography (CBCT), dose accumulation from plan adaptations, irradiation time per voxel accumulation, cumulative dose rate per voxel, and beam overlap per voxel, for example. Voxel-based treatment planning may be performed based on the correlation of 3D voxel recording of physical parameters (e.g., dose, dose rate, irradiation time) to 3D-voxel based output. Input data that is not 3D, such as tumor size, patient-reported outcome, survival, local control, biomarkers, patient medical history and demographic information, previous radiotherapy treatment data, cellular/biological timescales associated with disease presentation, cancer location, and cellular lifecycle (e.g., radiosensitivity) may also be included in the input data 101. The input data 101 can be entered manual by a user, or automatically entered by the computer system according to a treatment plan or physical metrics tracked by a radiation therapy system.

The user-defined function or model 102 is used to generate the biological outcome map based on a relationship (e.g., correlation) between the physical parameter input and a biological outcome on a per-voxel basis. For example, the user-defined function 102 can be based on a biological model representing the relationship between irradiation time and toxicity (e.g., the toxicity increases over time in correlation with irradiation time), higher dosage rates correlated with lower toxicity, and higher levels of biomarkers correlated with increased global radio sensitivity. Moreover, embodiments of the present invention enable the output data 103 to be stored more accurately compared to traditional techniques. For example, toxicities over time can be stored along with computerized tomography (CT)/magnetic resonance imaging (MRI)/positron emission tomography (PET) based cellular damage and tumor response per voxel. Advantageously, embodiments of the present invention enable accurate inputs 101 to be correlated with accurate outputs 103 based on biological models of user-defined functions 102. The user-defined functions 102 can be based on toxicity, systemic or genetic biomarkers, radio sensitivity, imaging information (anatomical, functional, molecular), and Flash effect, for example.

Figure 2:
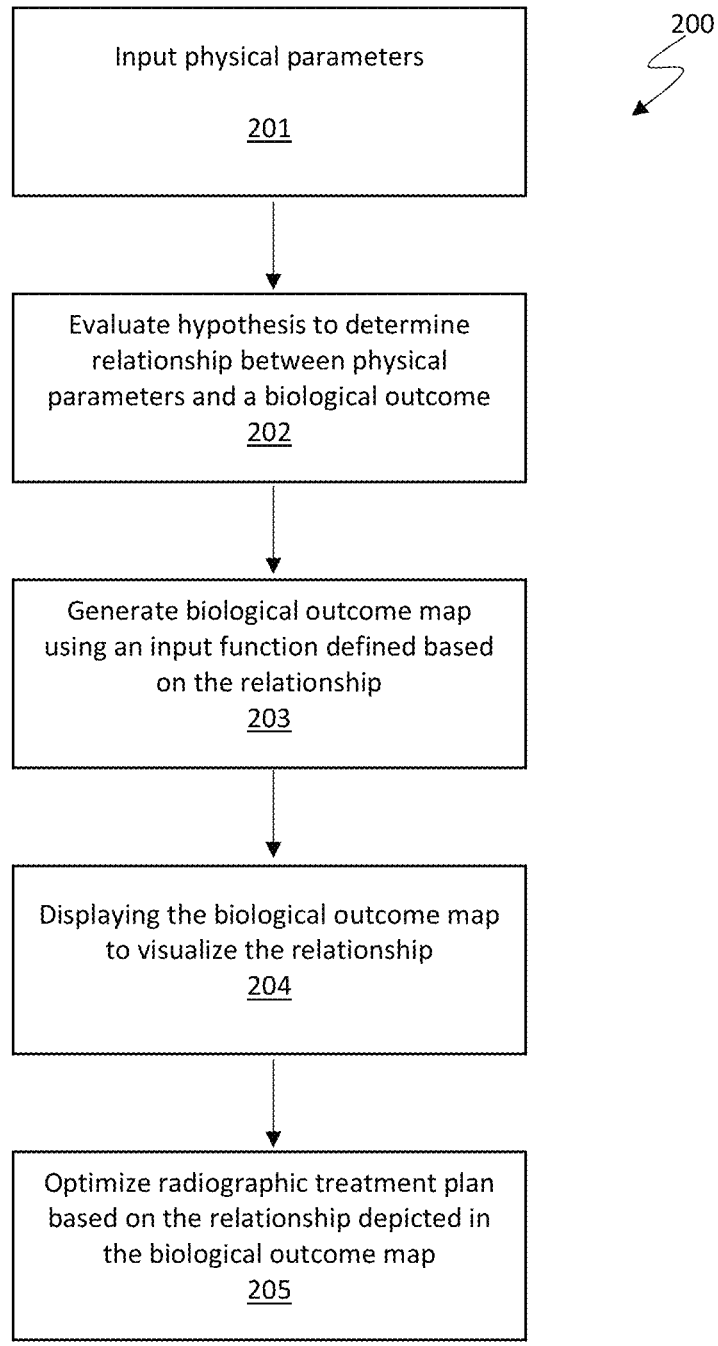
FIG. 2 is a flowchart depicting an exemplary sequence of computer implemented steps for performing biological planning based on physical input parameters and a biological model according to embodiments of the present invention.

With regard to FIG. 2, an exemplary sequence of computer implemented steps to realize process 200 for performing biological planning based on physical input parameters and a biological model is depicted according to embodiments of the present invention. The steps may be realized as program code stored in memory and executed by a computer processor. At step 201, recorded physical parameters are received as input. The physical parameters may include a recorded dose, a dose rate, an irradiation time, and/or a beam overlap, for example, and the physical parameters may be associated with voxels of a treatment map. According to some embodiments, step 201 includes recording/accumulating physical input parameters over time, such as dose accumulation, irradiation time per voxel accumulation, and/or cumulative dose rate per voxel. The input data can be entered manual by a user, or automatically entered by a computer system according to a treatment plan or physical metrics tracked by a radiation therapy system.

At step 202, a hypothesis (e.g., a clinical research hypothesis) is tested to correlate input parameters with a biological parameter or outcome. For example, step 202 can include correlating the irradiation time of a voxel with the toxicity level (outcome) of the voxel. According to some embodiments, the biological outcome is determined by evaluating post-treatment images or other data. For example, radiomic techniques known in the art may be used to automatically associate the post-treatment image with biological outcome values for evaluating the hypothesis or model.

At step 203, a biological outcome map is generated to assign each voxel of the treatment map with a value (e.g., a toxicity score) based on an input function representing a biological model. At step 204, the biological outcome map is displayed on a display device to visualize the relationship (e.g., correlation) between the input parameter and the biological parameter or outcome. For example, the biological outcome map can be overlaid on top of a 3D dose map to visualize the relationship and differences between the biological outcome map and the 3D dose map. According to some embodiments, a time component is included at step 204 to generate a 4D video map of the events occurring over time. At step 205, the treatment planning process is optimized based on the correlation depicted in the biological outcome map. According to some embodiments, optimizing the radiotherapy treatment plan includes optimizing or adjusting a physical dose and a biological dose of the radiotherapy treatment plan. Moreover, some embodiments further assign priority levels to the physical dose and the biological dose based on the biological outcome map.

Exemplary Computer System

Embodiments of the present invention are drawn to computer systems for planning and optimizing a radiotherapy treatment plan by visualizing and quantifying correlations arising from tested hypotheses. The following discussion describes such exemplary computer systems.

Figure 3:
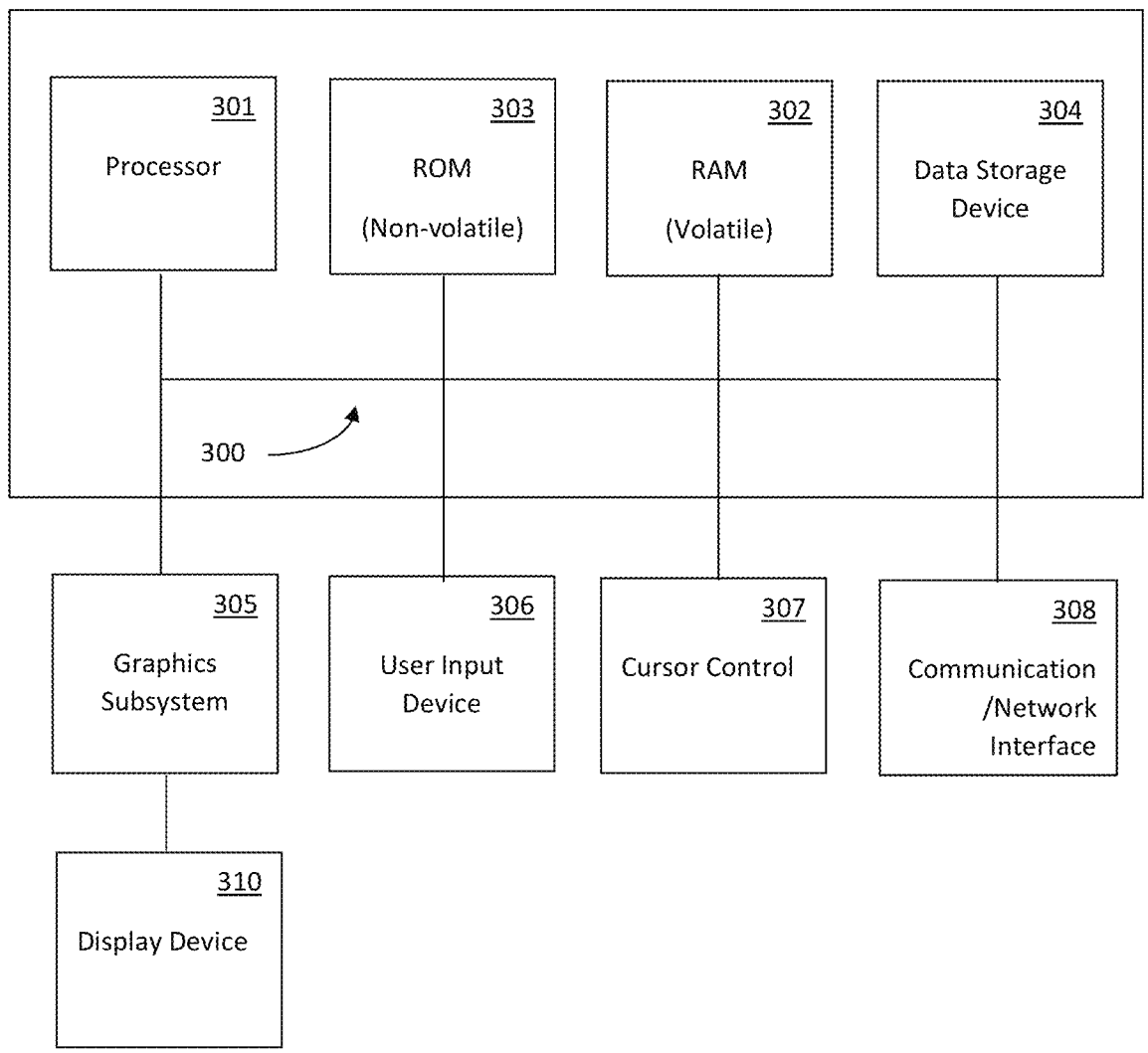
FIG. 3 is a block diagram depicting an exemplary computer system upon which embodiments of the present invention can be implemented.

In the example of FIG. 3, the exemplary computer system 312 includes a central processing unit (CPU) 301 for running software applications (e.g., a workload management application) and optionally an operating system. Random access memory 302 and read-only memory 303 store applications and data for use by the CPU 301. Data storage device 304 provides non-volatile storage for applications and data and may include fixed disk drives, removable disk drives, flash memory devices, and CD-ROM, DVD-ROM or other optical storage devices. The optional user inputs 306 and 307 comprise devices that communicate inputs from one or more users to the computer system 312 (e.g., mice, joysticks, cameras, touch screens, and/or microphones).

A communication or network interface 308 allows the computer system 312 to communicate with other computer systems, networks, or devices via an electronic communications network, including wired and/or wireless communication and including an Intranet or the Internet. The display device 310 may be any device capable of displaying visual information in response to a signal from the computer system 312 and may include a flat panel touch sensitive display, for example. The components of the computer system 312, including the CPU 301, memory 302/303, data storage 304, user input devices 306, and graphics subsystem 305 may be coupled via one or more data buses 300.

In the embodiment of FIG. 3, a graphics subsystem 305 is optional and may be coupled with the data bus and the components of the computer system 312. The graphics system 305 may comprise a physical graphics processing unit (GPU) and graphics/video memory. GPU may include one or more rasterizers, transformation engines, and geometry engines, and generates pixel data from rendering commands to create output images. The physical GPU can be configured as multiple virtual GPUs that may be used in parallel (e.g., concurrently) by a number of applications or processes executing in parallel, or multiple physical GPUs may be used simultaneously. Graphics subsystem 305 can output display data to display device 310, for example, to visualize correlations and/or differences between biological outcomes of a tested hypothesis rendered in 3D and a 3D dose map as discussed above.

A Model-Based PBS Optimization for Flash Therapy Treatment Planning and Oncology Information System Embodiments of the present invention implement Quantitative Time-Dependent Model-Based Charged Particle Pencil Beam Scanning Optimization for FLASH therapy. Embodiments of the present invention implement intensity modulated charged particle Pencil Beam Scanning optimization of local time-dependent particle flux to attain desired properties of quantitative time-dependent biological/chemical/physical models at various points within a patient receiving radiation therapy.

As described above, ultra-high dose rate radiotherapy, or FLASH therapy, delivers high doses of radiation at very high-speed achieving dose rates of 40 Gy/s and above. Pre-clinical studies have shown that delivering radiotherapy at such ultra-high dose rates allows comparable tumor control while sparing the healthy tissue thereby reducing toxicities.

As described above, the optimal characteristics of radiation treatment delivery for FLASH are not currently known because a mechanism of action has not yet been proven. However, it is useful to compute an optimal treatment delivery based on hypothesized methods of action. One such example, the oxygen depletion hypothesis, has shown promise as a possible explanation. Based on this hypothesis, it is in principle possible to model levels of indirect cell damage from free radicals created by incident radiation. More specifically, given an appropriate time-dependent instantaneous particle flux, it is possible to simulate oxygen depletion and re-oxygenation and thereby quantify the levels of indirect damage produced by free radicals. However, the appropriate time-dependent flux pattern that simultaneously minimizes indirect damage yet still delivers therapeutic dose to a target is not known, nor is there a system to optimize charged particle delivery parameters to create such a pattern. Embodiments of the present invention implement a system to optimize parameters of charged particle delivery to attain a desired state of a quantitative time-dependent biological/physical/chemical model based on a known or hypothesized mechanism of action for normal tissue sparing.

Embodiments of the present invention implement an optimization algorithm that requires a biological/physical/chemical model whose inputs are time-dependent flux (e.g., instantaneous particles per second as a function of time down to the nanosecond scale, or below) and whose outputs are some measure of a desired outcome. Embodiments of the present invention can advantageously implement a model that computes indirect cell damage, for a given tissue type, as a function of free radical production governed by time dependent oxygen concentration and particle flux. The optimizer would then find the optimal (e.g., best) combination of time-depended pencil beam scanning parameters (e.g., energy, flux, spot or scan-line delivery pattern) to simultaneously minimize the levels of free radical production, in various healthy tissue types, and maximize the therapeutic dose to the target.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A computer-implemented method comprising:
receiving an input parameter for each voxel of a plurality of voxels of a treatment map, wherein the input parameter is included in a radiotherapy treatment plan;
generating a biological outcome map that assigns a respective value to said each voxel of the treatment map, wherein the respective value for said each voxel is based on a model that relates a value of the input parameter for said each voxel to a biological outcome for said each voxel; and
modifying the radiotherapy treatment plan based on the respective value for said each voxel comprised in the biological outcome map, wherein said modifying comprises adjusting the value of the input parameter to modify the respective value for said each voxel;
wherein said modifying further comprises implementing quantitative time-dependent model-based charged particle pencil beam scanning optimization for FLASH therapy.

2. The method of claim 1, further comprising determining the respective value for said each voxel using an input function that represents the model.

3. The method of claim 1, wherein said modifying the radiotherapy treatment plan comprises reducing a dose delivered to normal tissue.

4. The method of claim 1, wherein said modifying the radiotherapy treatment plan comprises optimizing a physical dose and a biological dose of the radiotherapy treatment plan, the method further comprising assigning priority levels to the physical dose and the biological dose.

5. The method of claim 1, wherein the input parameter is selected from the group consisting of: a dose, a dose rate, an irradiation time, and a beam overlap.

6. The method of claim 1, wherein the biological outcome is selected from the group consisting of: a toxicity level, a systemic biomarker, and a genetic biomarker.

7. The method of claim 1, further comprising optimizing parameters of charged particle delivery to attain a desired state of a quantitative time-dependent model based on a mechanism of action for normal tissue sparing.

8. The method of claim 1, further comprising measuring instantaneous particles per nanosecond as a function of time.

9. The method of claim 1, further comprising implementing an optimization algorithm using a model that uses time-dependent flux as an input.

10. The method of claim 9, wherein the optimization algorithm implements a model that computes indirect cell damage, for a given tissue type, as a function of free radical production governed by time dependent oxygen concentration and particle flux.

11. The method of claim 9, wherein the optimization algorithm models levels of indirect cell damage from free radicals created by incident radiation.

12. The method of claim 9, wherein the optimization algorithm simulates oxygen depletion and re-oxygenation using a time-dependent instantaneous particle flux.

13. An electronic system comprising:
a memory; and
a processor in communication with the memory, wherein the processor is operable to execute instructions for performing a method comprising:
receiving an input parameter for each voxel of a plurality of voxels of a treatment map, wherein the input parameter is included in a radiotherapy treatment plan;
generating a biological outcome map that assigns a respective value to said each voxel of the treatment map, wherein the respective value for said each voxel is based on a model that relates a value of the input parameter for said each voxel to a biological outcome for said each voxel; and
modifying the radiotherapy treatment plan based on the respective value for said each voxel comprised in the biological outcome map, wherein said modifying comprises adjusting the value of the input parameter to modify the respective value for said each voxel;
wherein said modifying further comprises implementing quantitative time-dependent model-based charged particle pencil beam scanning optimization for FLASH therapy.

14. The system of claim 13, wherein said modifying the radiotherapy treatment plan comprises reducing a dose delivered to normal tissue.

15. The system of claim 13, wherein the method further comprises optimizing parameters of charged particle delivery to attain a desired state of a quantitative time-dependent biological/physical/chemical model based on a mechanism of action for normal tissue sparing.

16. The system of claim 13, wherein the input parameter is selected from the group consisting of: a dose, a dose rate, an irradiation time, and a beam overlap.

17. The system of claim 13, wherein the biological outcome is selected from the group consisting of: a toxicity level, a systemic biomarker, and a genetic biomarker.

18. A non-transitory computer-readable storage medium embodying instructions that are executed by a processor to cause the processor to perform a method comprising:
receiving an input parameter for each voxel of a plurality of voxels of a treatment map, wherein the input parameter is included in a radiotherapy treatment plan;
generating a biological outcome map that assigns a respective value to said each voxel of the treatment map, wherein the respective value for said each voxel is based on a model that relates a value of the input parameter for said each voxel to a biological outcome for said each voxel; and
modifying the radiotherapy treatment plan based on the based on the respective value for said each voxel comprised in the biological outcome map, wherein said modifying comprises adjusting the value of the input parameter to modify the respective value for said each voxel;
wherein said modifying further comprises implementing quantitative time-dependent model-based charged particle pencil beam scanning optimization for FLASH therapy.

19. The non-transitory computer-readable storage medium of claim 18, wherein said modifying the radiotherapy treatment plan comprises reducing a dose delivered to normal tissue.

20. The non-transitory computer-readable storage medium of claim 18, wherein the method further comprises optimizing parameters of charged particle delivery to attain a desired state of a quantitative time-dependent biological/physical/chemical model based on a mechanism of action for normal tissue sparing.

21. The non-transitory computer-readable storage medium of claim 18, wherein the input parameter is selected from the group consisting of: a dose, a dose rate, an irradiation time, and a beam overlap.

22. The non-transitory computer-readable storage medium of claim 18, wherein the biological outcome is selected from the group consisting of: a toxicity level, a systemic biomarker, and a genetic biomarker.

\* \* \* \* \*